US010587038B2

(12) United States Patent
Cappa et al.

(10) Patent No.: US 10,587,038 B2
(45) Date of Patent: Mar. 10, 2020

(54) SYSTEMS AND METHODS FOR AN ANTENNA OF AN IMPLANTABLE ELECTRONIC DEVICE

(71) Applicant: PACESETTER, INC., Sylmar, CA (US)

(72) Inventors: Armando M. Cappa, Granada Hills, CA (US); Jorge N. Amely-Velez, Simi Valley, CA (US); Alan B. Vogel, Santa Clarita, CA (US); Wisit Lim, Santa Clarita, CA (US); John R. Gonzalez, McKinney, TX (US); Alexander Robertson, Los Angeles, CA (US); Alex Soriano, Ventura, CA (US); Evan Sheldon, Sherman Oaks, CA (US); Perry Li, Arcadia, CA (US); Jeffery Crook, Belmont, CA (US)

(73) Assignee: Pacesetter, Inc., Sylmar, CA (US)

( * ) Notice: Subject to any disclaimer, the term of this patent is extended or adjusted under 35 U.S.C. 154(b) by 201 days.

(21) Appl. No.: 15/633,614

(22) Filed: Jun. 26, 2017

(65) Prior Publication Data

US 2018/0131085 A1    May 10, 2018

Related U.S. Application Data

(60) Provisional application No. 62/419,868, filed on Nov. 9, 2016.

(51) Int. Cl.
*H01Q 1/27*    (2006.01)
*H01Q 1/38*    (2006.01)
(Continued)

(52) U.S. Cl.
CPC ........... *H01Q 1/38* (2013.01); *A61N 1/37229* (2013.01); *H01Q 1/22* (2013.01); *H01Q 1/273* (2013.01);
(Continued)

(58) Field of Classification Search
CPC ............ H01Q 1/38; H01Q 1/273; H01Q 1/22; H01Q 9/40; H01Q 9/42; H01Q 5/364; A61N 1/37229
See application file for complete search history.

(56) References Cited

U.S. PATENT DOCUMENTS

2005/0203583 A1* 9/2005 Twetan ............... A61N 1/37229
607/36
2009/0266573 A1* 10/2009 Engmark ............... A61N 1/375
174/50.54

(Continued)

OTHER PUBLICATIONS

Extended EP Search Report—European Counterpart EP App No. 18179737.4.

*Primary Examiner* — Hoang V Nguyen
*Assistant Examiner* — Awat M Salih
(74) *Attorney, Agent, or Firm* — Polsinelli PC

(57) ABSTRACT

Disclosed herein is an implantable electronic device having a housing containing an electrical circuit. The implantable electronic device further includes an antenna assembly coupled to the electrical circuit. The antenna assembly has an antenna with a dielectric antenna body within which an antenna trace is disposed. Portions of the antenna trace are disposed in offset transverse layers in a non-overlapping arrangement, thereby reducing capacitive coupling between the layers of the antenna trace. In certain implementations, the antenna assembly has one or more capacitive features that selectively overlap portions of the antenna trace and facilitate tuning of the antenna.

15 Claims, 13 Drawing Sheets

(51) Int. Cl.
*H01Q 1/22* (2006.01)
*A61N 1/372* (2006.01)
*H01Q 9/40* (2006.01)
*H01Q 5/364* (2015.01)
*H01Q 9/42* (2006.01)

(52) U.S. Cl.
CPC .............. *H01Q 5/364* (2015.01); *H01Q 9/40* (2013.01); *H01Q 9/42* (2013.01)

(56) References Cited

U.S. PATENT DOCUMENTS

| | | |
|---|---|---|
| 2010/0114246 A1 | 5/2010 | Yamamoto et al. |
| 2012/0276854 A1 | 11/2012 | Himanshu et al. |
| 2014/0002314 A1* | 1/2014 | Li .......................... H01Q 1/36 343/702 |
| 2015/0077208 A1 | 3/2015 | Goldman et al. |
| 2015/0096167 A1 | 4/2015 | Zhao et al. |
| 2018/0131085 A1 | 5/2018 | Cappa et al. |

* cited by examiner

SYSTEMS AND METHODS FOR AN ANTENNA OF AN IMPLANTABLE ELECTRONIC DEVICE

CROSS REFERENCE TO RELATED APPLICATIONS

This application claims the benefit of U.S. Provisional Patent Application Ser. No. 62/419,868, filed Nov. 9, 2016.

FIELD OF THE INVENTION

Aspects of the present invention relate to medical apparatus and methods. More specifically, the present invention relates to systems and methods for implementing an antenna on an implantable medical device.

BACKGROUND OF THE INVENTION

Implantable pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems, commonly include a hermetically sealed housing, feedthrough pins, and a connector assembly that is enclosed in a header. Electrical stimulation originating in the housing is led to the connector assembly through feedthrough pins. The connector assembly serves to transmit electrical signals out of the IPG and to a lead electrically connected to the connector assembly, the lead transmitting electrical signals between the IPG and patient tissue. Certain IPGs are further adapted to sense tissue activity, such as intrinsic heart activity, of a patient.

The connector assembly of an IPG generally includes a wide range of components including, without limitation, lead connectors, feedthrough pins, and conductors for coupling the lead connectors to the feedthrough pins. The header may further house an antenna for enabling wireless communication between the electrical circuitry of the IPG and external computing devices. Such computing devices may be used, among other things, to configure settings of the IPG, to perform tests and other diagnostics of IPG components, and to collect performance data that is measured and stored by the IPG during operation.

With the quantity and size of components maintained within the header, space is at a premium and critical components, such as lead connectors, are often given priority over antennas with regards to header space. As a result of such space limitations, antennas for use in IPGs are often limited in their length and communication capabilities.

Accordingly, there is a need in the art for systems and methods directed to antennas suitable for use within the limited space of an IPG header.

BRIEF SUMMARY OF THE INVENTION

The implantable electrical devices and methods disclosed herein include antenna assemblies adapted for use in the relatively limited space available within an implantable electrical device header. In one embodiment, a first implantable electronic device including a hermetically sealed housing containing an electrical circuit further includes an antenna assembly coupled to the electrical circuit. The antenna assembly defines a longitudinal axis and includes an antenna. The antenna includes a dielectric antenna body extending along the longitudinal axis within which an antenna trace is disposed. The antenna trace includes a first trace portion disposed in a first transverse layer and defining a first trace path, a second trace portion disposed in a second transverse layer longitudinally offset from the first transverse layer and defining a second trace path, and a junction extending longitudinally, at least in part, and coupling the first trace portion to the second trace portion. When projected to be coplanar, the first trace path defines a trace boundary within which the second trace path is contained.

In one implementation of the present disclosure, the antenna further includes a capacitive feature that extends from at least one of the first or second trace portions to at least partially overlap the second or first trace portion, respectively, with a portion of the antenna body disposed therebetween. In a corresponding implementation, the capacitive feature includes a tab extending from the first or second trace portion.

In another implementation, each of the dielectric antenna body and the antenna trace are composed of a biocompatible material. For example, the dielectric antenna body may be composed of one of alumina ceramic, liquid crystal polymer, and perovskite ceramic and the antenna trace may be composed of gold or platinum.

In yet another implementation, the implantable electronic device includes a feedthrough pin electrically coupled to the electrical circuit and extending through the housing and the antenna assembly further includes a mounting arm electrically coupled to each of the antenna trace and the feedthrough pin. In certain related implementations, the antenna includes a transverse surface and the mounting arm includes a coupling feature extending across the transverse surface. In such implementations, a capacitive feature may be disposed between the coupling feature and the transverse surface such that the capacitive feature overlaps one of the first trace portion or the second trace portion with a portion of the antenna body disposed therebetween. The antenna assembly may further include a shroud coupled to each of the antenna body and a terminal end of the mounting arm, the shroud defining a receptacle into which the mounting arm is inserted.

In still another implementation, the antenna trace may further include a third trace portion disposed in a third transverse layer of the antenna body and defining a third trace path. In such implementations, the transverse layers are arranged such that the second transverse layer is disposed between the first and third layers. Also, if projected to be coplanar, the second trace path defines a second trace boundary within which the third trace path is contained.

In another embodiment, an implantable electronic device includes a first implantable electronic device including a hermetically sealed housing containing an electrical circuit further includes an antenna assembly coupled to the electrical circuit. The antenna assembly includes a dielectric antenna body defining a longitudinal axis and an antenna trace disposed within the antenna body and arranged in a plurality of transverse trace layers. The trace layers are shaped and arranged to reduce the capacitive coupling between the trace layers relative to an arrangement in which the trace layers are all overlapping. The antenna assembly further includes at least one capacitive feature. Each capacitive feature overlaps a respective portion of the antenna trace such that a corresponding portion of the antenna body is disposed therebetween.

In one implementation of the present disclosure, the capacitive feature extends from a first layer of the plurality of trace layers and overlaps a second layer of the plurality of trace layers.

In another implementation, the implantable electronic device further includes a feedthrough pin coupled to the electrical circuit and extending through the housing and the antenna assembly further includes a mounting arm that electrically couples the feedthrough pin to the antenna trace. In certain embodiments, the capacitive feature includes a plate coupled to the mounting arm.

In yet another embodiment, each trace layer of the plurality of trace layers defines a respective trace path and a respective trace boundary. Further, the trace layers are ordered such that, if projected to be coplanar, each respective trace path is within the respective trace boundary of a preceding trace layer.

In yet another embodiment, a method of manufacturing an implantable electronic device is provided. The method includes forming an antenna by delivering an antenna trace within a dielectric antenna body. The antenna trace includes a first trace portion disposed in a first transverse layer and defining a first trace path and a second trace portion disposed in a second transverse layer longitudinally offset from the first transverse layer and defining a second trace path. If projected to be coplanar, the first trace path defines a trace boundary and the second trace path is within the trace boundary.

In one implementation, the method further includes tuning the antenna by forming one or more capacitive features that at least partially overlap at least one of the first trace portion or the second trace portion such that a portion of the antenna body is disposed therebetween. In a corresponding implementation, the capacitive features extend from the first trace portion to partially overlap the second trace portion and/or extend from the second trace portion to partially overlap the first trace portion.

In another implementation, the implantable electronic device includes a feedthrough pin. The method further includes coupling the antenna to a conductive mounting arm and coupling the mounting arm to the feedthrough pin such that the mounting arm electrically couples the antenna to the feedthrough pin. In such implementations, the method may further include tuning the antenna by coupling a capacitive feature to the mounting arm such that the capacitive feature overlaps at least one of the first trace portion or the second trace portion with a portion of the antenna body disposed therebetween.

DETAILED DESCRIPTION

Figure 1:
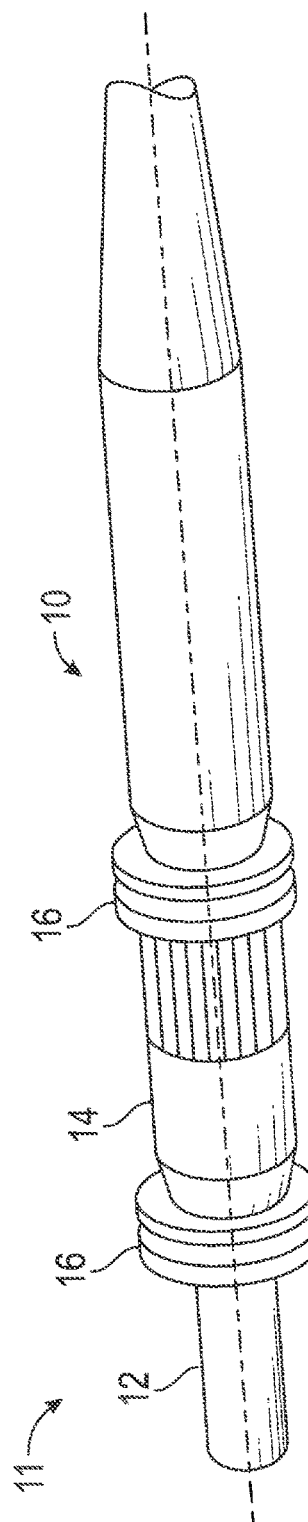
FIG. 1 is an isometric view of a proximal end portion (i.e., lead connector end) of a conventional transvenous bipolar pacing lead.

Implementations of the present disclosure involve an implantable pulse generator (IPG) for administering electrotherapy or other neurostimulation via an implantable lead having a lead connector end on a proximal end of the implantable lead. The IPG includes a housing or can and a connector assembly enclosed in a header, both of which are coupled to the housing or can. The header and connector assembly combine to form at least one lead connector receiving bore or receptacle that includes electrical contacts that make electrical contact with corresponding electrical terminals on the lead connector end on the proximal end of the implantable lead when the lead connector end is plugged into or otherwise received in the lead connector receiving bore or receptacle. Via the electrical connection between the corresponding electrical terminals of the lead connector end and the electrical contacts of the lead connector receiving bore, electrical signals can be administered from the IPG and through the lead to patient tissue. Similarly, but in reverse, electrical signals originating in patient tissue can travel via the lead to the IPG to be sensed at the IPG.

In conventional IPGs, space within the header is limited. The wide range of parts associated with the connector assembly, in particular, requires a significant portion of the space within the header. Notably, many parts associated with the connector assembly are unable to be eliminated or miniaturized. For example, standards, and regulations often dictate the minimum sizes of leads and lead connectors. Many such standards and regulations are rooted in practical considerations regarding a doctor or surgeon's ability to manipulate the components while wearing gloves and while handling the components in a wet environment. Accordingly, the dimensions of an antenna within the header are often limited by the space considerations other components.

To address the size limitations imposed by IPG headers, antennas and antenna assemblies in accordance with this disclosure include antenna bodies composed of dielectric materials within which an antenna trace is disposed. The antenna is generally coupled to a conductive mounting arm that mounts to a feedthrough pin extending out of the IPG housing.

Antennas in accordance with this disclosure include traces distributed within the antenna body in multiple transverse trace layers. Each layer of the antenna trace is shaped to be non-overlapping with the other trace layers. More specifically, the trace layers are arranged such that successive trace layers define progressively decreasing boundaries that encompass the boundaries of subsequent trace layers. As a result, a long antenna length can be accommodated while reducing the capacitive coupling between adjacent trace layers.

Tuning of the antenna may be achieved by selective placement of capacitive features within the antenna. In certain implementations, the capacitive features are tabs or similar structures that extend from one layer of the antenna trace to overlap a portion of a second layer of the antenna trace such that a portion of the antenna body is disposed between the tab and the portion of the second layer. In other implementations, the capacitive feature is a plate or tab coupled to the mounting arm such that the plate or tab overlaps a portion of a trace layer. In either case, a capacitive structure is formed in which the capacitive feature forms a first plate, the overlapped antenna trace portion forms a second plate, and the portion of the antenna body acts as the dielectric between the two plates. By adjusting the amount of overlap between the capacitive feature and the trace layer, the material of the antenna body, and the distance between the capacitive feature and the overlapped trace layer, the capacitance of the capacitive structure and, as a result, the performance characteristics of the antenna may be tuned to suit a particular application.

Before beginning a detailed discussion of the antenna and antenna assembly, a general discussion is first given regarding features of a common lead connector end at the proximal end of an implantable medical lead followed by a general discussion of the features of an IPG. While the teachings disclosed herein are given in the context of an IPG, the teachings are equally applicable to implantable medical monitors (e.g., implantable cardiac monitors) or any other implantable electronic device employing an antenna assembly.

FIG. 1 shows a proximal end portion 10 of a conventional transvenous, bipolar pacing lead, but is generally representative of any type of implantable lead whether in the cardiac, pain management, deep brain stimulation, or other medical treatment space. The diameter of such a lead may be made a sufficiently small diameter to facilitate the lead's implantation into small veins such as those found in the coronary sinus region of the heart and to allow implantation of a plurality of leads into a single vessel for multi-site or multi-chamber pacing. It should be understood, however, that other lead designs may be used, for example, mulitpolar leads having proximal end portions that are bifurcated, trifurcated or have other branched configurations. While the lead whose proximal end is shown in FIG. 1 is of the bipolar variety, there are unipolar leads that carry but a single electrode, and multipolar leads that have more than two electrodes.

As is well known in the art, bipolar coaxial leads typically consists of a tubular housing of a biocompatible, biostable insulating material containing an inner multifilar conductor coil that is surrounded by an inner insulating tube. The inner conductor coil is connected to a tip electrode on the distal end of the lead. The inner insulating tube is surrounded by a separate, outer multifilar conductor coil that is also enclosed within the tubular housing. The outer conductor coil is connected to an anodal ring electrode along the distal end portion of the lead. The inner insulation is intended to electrically isolate the two conductor coils preventing any internal electrical short circuit, while the housing protects the entire lead from the intrusion of body fluids. These insulating materials are typically either silicone rubber or polyurethane. More recently, there have been introduced bipolar leads in which multifilar cable conductors contained within multilumen housings are substituted for the conductor coils in order to reduce even further the overall diameter of the lead.

The proximal lead end portion 10 shown in FIG. 1 includes a lead connector end 11 that conforms to the IS-1 standard, comprising a pair of coaxial spaced-apart electrical terminals including a tip terminal 12 and a ring terminal 14. The tip terminal 12 is electrically connected by means of the inner conductor coil to the tip electrode at the distal end of the lead, while the ring terminal 14 is electrically connected to the anodal ring electrode by means of the outer conductor coil. The tip and ring terminals of the lead connector end may each be engaged by a conductive garter spring contact or other resilient electrical contact element in a corresponding lead connector receiving bore of the header, the resilient electrical contact element being carried by a connector assembly enclosed in the header as described below. The lead connector end 11 on the proximal lead end portion 10 further comprises spaced-apart pairs of seal rings 16 for abutting against in a fluid-sealing manner the inner circumferential surface of the lead connector receiving bore of the header, thereby preventing body fluids from reaching the electrical terminals and contacts when the lead connector end 11 is plugged into the corresponding lead connector receiving bore. With the lead connector end 11 of the lead inserted in the lead connector receiving bore of the header and connector assembly, the tip and ring terminals 12 and 14 are electrically coupled via the contacts of the connector assembly and a feedthrough to the electronic circuits within the hermetically sealed housing of the IPG (e.g., cardiac pacemaker. ICD, or other implantable tissue stimulation and/or sensing device such as those used in pain management, etc.).

Figure 2:
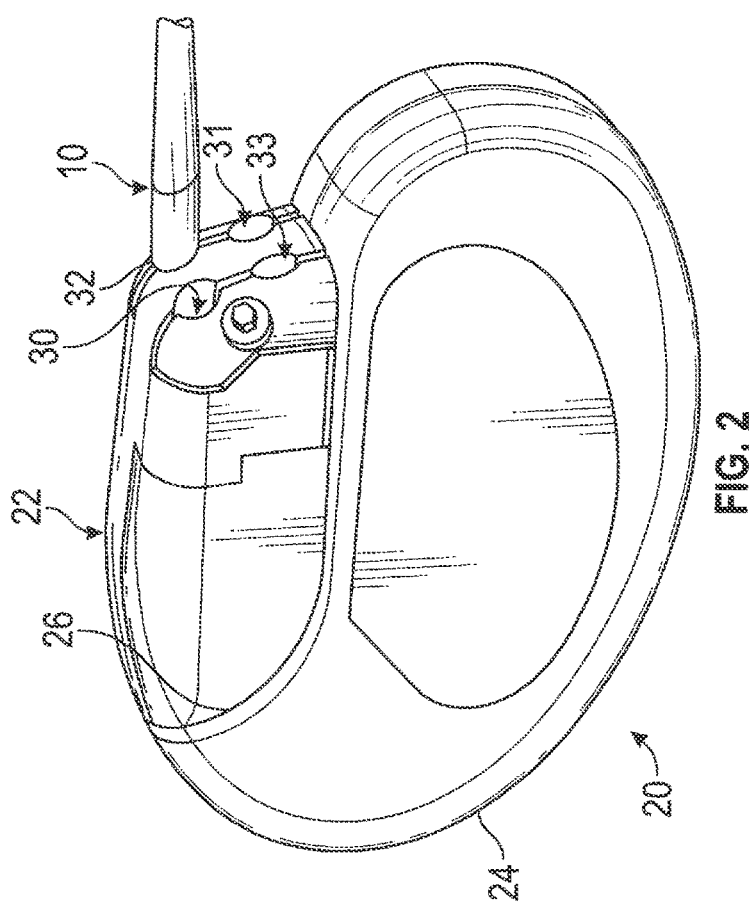
FIG. 2 is an isometric view of a cardiac pacemaker/defibrillator unit (i.e., implantable pulse generator (IPG)) incorporating connector junctions or terminals for communication with one or more electrodes.

FIG. 2 shows an IPG 20 that may be, among other devices, a multi-site or multi-chamber cardiac pacemaker/defibrillator unit. The IPG 20 is generally representative of any type of IPG incorporating a header connector assembly 22 coupled to a housing 24. The header connector assembly 22 includes a header 40 enclosing a connector assembly 42, both of which are depicted respectively in FIGS. 3A and 3B discussed below. The IPG 20 is of a conventional design, including a hermetically sealed housing 24, which is also known as a can or casing. The housing 24 encloses the electronic components of the IPG 20 with the header connector assembly 22 mounted along a top edge 26 of the housing 24.

FIG. 2 illustrates that, in some embodiments, the header connector assembly 22 may include four or more lead connector receiving bores or receptacles 30, 31, 32 and 33 for receiving the lead connector ends of four implantable leads. FIG. 2 also shows the proximal end portion 10 of a lead, wherein the lead connector end on the proximal end portion 10 of the lead is received in a corresponding receptacle 32. In other embodiments, the header connector assembly 22 includes two receptacles comprising a single pair of receptacles (i.e., receptacles 30 and 33) for receiving the proximal ends of leads such as, for example, conventional bipolar leads and/or conventional cardioverting and/or defibrillating leads.

Figure 3A:
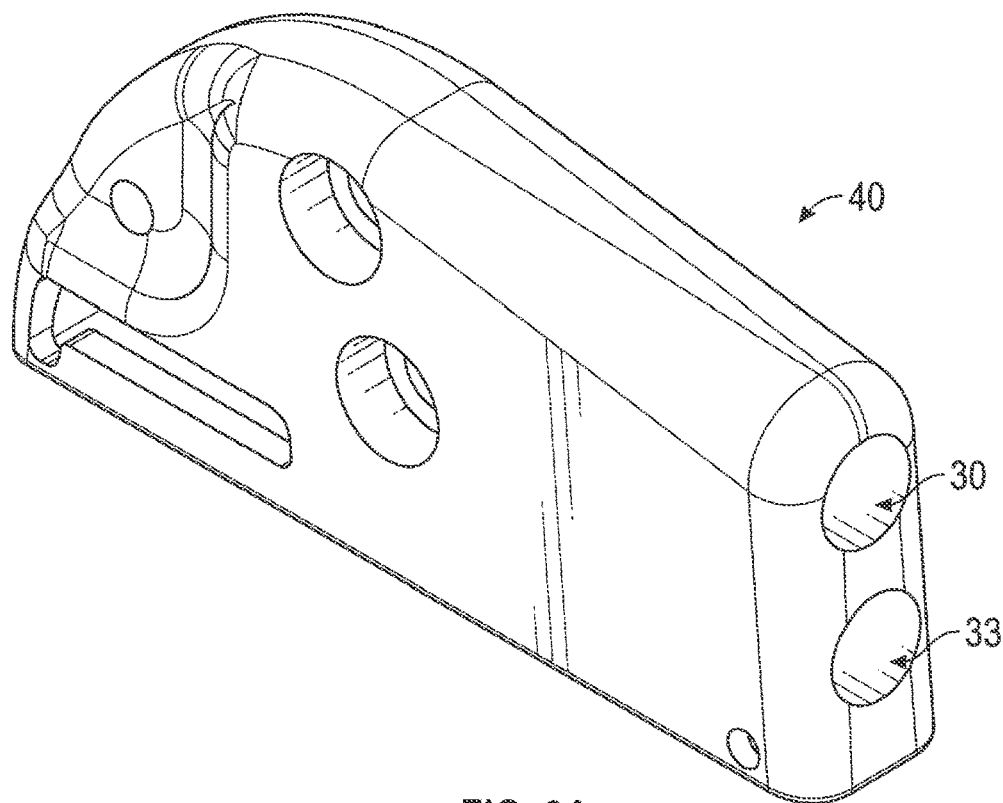
FIG. 3A is an isometric view of a representative header.
Figure 3B:
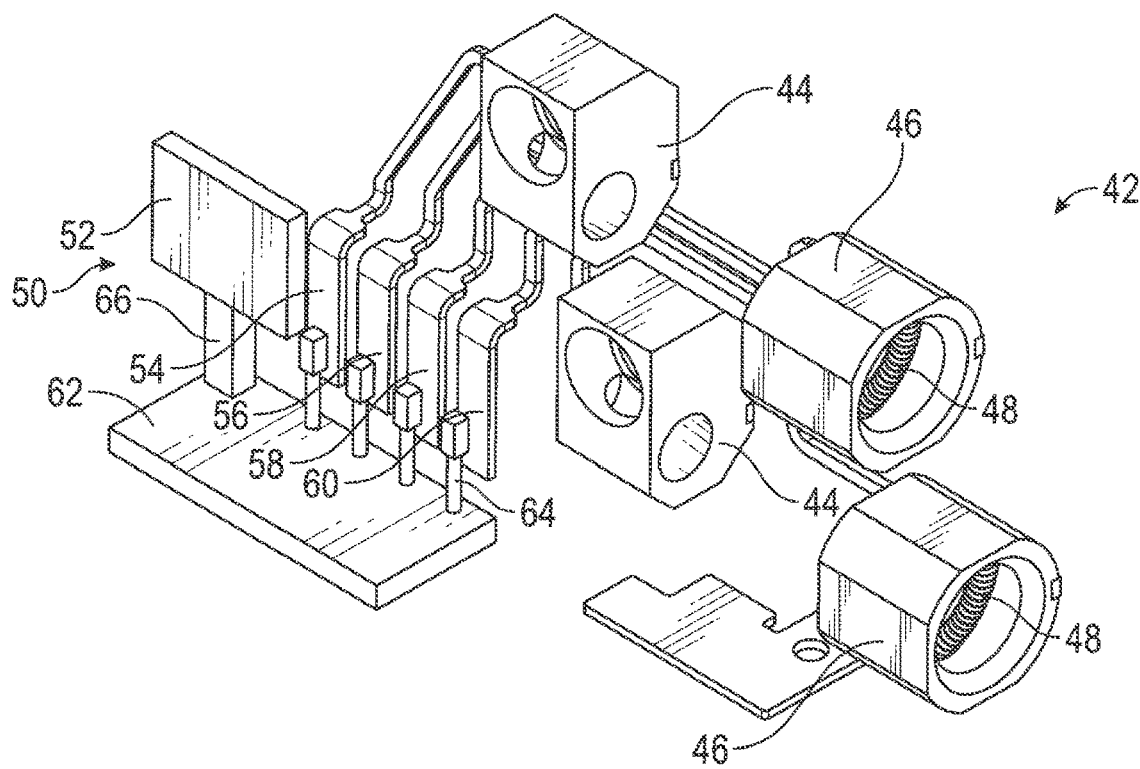
FIG. 3B is an isometric view of a representative connector assembly and first antenna assembly used within the header of FIG. 3A to form a header connector assembly.

FIG. 3A is an isometric view of a representative header 40 and FIG. 3B is an isometric view of a representative connector assembly 42 and antenna assembly 50. Unlike the header connector assembly 22 of FIG. 2, the header 40 of FIG. 3A only has a single pair of receptacles 30 and 33.

However, in other embodiments, the header 40 of FIG. 3A may have two or more pairs of receptacles similar to the embodiment of FIG. 2.

As illustrated in FIG. 3B, the connector assembly 42 includes tip blocks 44 and ring blocks 46. The ring blocks 46 include spring contacts 48. Each electrical block 44 and 46 of the connector assembly 42 serves as an electrical contact of the connector assembly 42. Thus, as can be understood from FIGS. 1, 2 and 3B, each tip block 44 is configured to receive and make electrical contact with the tip terminal 12 of a lead connector end 11 received in the corresponding receptacle 30, 33 of the header 40. Similarly, each ring block 46 is configured to receive and make electrical contact with the ring terminal 14 of a lead connector end 11 received in the corresponding receptacle 30, 33 of the header 40. While the connector assembly 42 of FIG. 3B is of an IS-1 configuration, other configurations (e.g., IS-4, etc.) are used in other embodiments. While the connector assembly 42 of FIG. 3B only depicts two pairs of blocks 44, 46, in other embodiments where the header includes more than a single pair of receptacles 30, 33 (e.g., two pairs of receptacles 30, 31, 32, 33 as indicated in FIG. 2), the connector assembly 42 will have a four pairs of blocks 44, 46.

As shown in FIG. 3B, the connector assembly 42 also includes an A-tip tab 54, an A-ring tab 56, an RV-ring tab 58, and an RV-tip tab 60 and other conductors that extend between the various tabs and their respective electrical contacts of the connector assembly 42 or other components thereof. The various tabs are welded or otherwise coupled to corresponding terminals extending from circuitry of the IPG 20 contained in the housing 24 of the IPG 20 depicted in FIG. 2 when the header connector assembly 22 is joined with the housing 24 to form the IPG 20. In the implementation illustrated in FIG. 3B, for example, the IPG 20 includes a pin bank 62 including multiple feedthrough pins, such as feedthrough pin 64. Each feedthrough pin is coupled to an electrical circuit within the IPG 20 and extends through the housing 24 of the IPG 20 while preserving the hermetic seal of the housing 24. The feedthrough pin is then welded or otherwise coupled to one of the tabs of the connector assembly 42. For example, the feedthrough pin 64 is coupled to the RV-tip tab 60. The connector assembly 42 is manufactured of materials and via methods known in the industry. The connector assembly 42 may be molded into the header 40 to form the header connector assembly 22 of FIG. 2, which can be considered a first module that is then anchored to a second module in the form of the housing 24. The header connector assembly 22 (i.e., first module) may be anchored to the housing 24 (i.e., the second module) via systems and methods known in the art.

The IPG 20 further includes an antenna assembly 50, which includes an antenna 52 coupled to a mounting arm 66. The mounting arm 66 is mounted to a pin (hidden within the mounting arm 66) of the pin bank 62. The antenna assembly 50 facilitates radio frequency (RF) communication between the IPG 20 and one or more external computing systems. Communication may occur using one or more proprietary or standard protocols including, without limitation, Wi-Fi, Bluetooth, Bluetooth low energy, Zigbee, and IEEE 802.15.4. Data received from an external computing device by the IPG 20 through the antenna assembly 50 may include, without limitation, one or more of commands, configuration data, and software/firmware updates. Data sent by the IPG 20 to an external computing device may include, without limitation, one or more of device settings of the IPG 20, patient data collected during operation of the IPG 20, and diagnostic data regarding functionality of the IPG 20.

FIGS. 4A-4D are schematic illustrations of a second embodiment of an IPG 120 including an antenna assembly 150 in accordance with this disclosure. The IPG 120 includes a hermetically sealed housing 124 coupled to a connector assembly 142. As shown in FIG. 3A, a cover (e.g., header 40) is generally disposed over the connector assembly 142, however, for purposes of clarity, such a cover is not included in FIGS. 4A-4D. The connector assembly 142 includes three connector blocks 144, 146, 148 adapted to receive terminals of leads (not shown). The connector block 144 includes two terminals 180, 182 adapted to make electrical contact with terminals of a lead inserted into the connector block 144. Similarly, the connector blocks 146, 148 each include four terminals (for example, connector block 146 includes terminals 184-190) similarly adapted to make electrical contact with terminals of a lead inserted into the connector blocks 146, 148. To facilitate communication between the connector blocks 144-148 and internal circuitry of the IPG 20, each terminal of the connector blocks 144-148 is connected by a conductor to a feedthrough pin of a feedthrough pin bank. For example, in the embodiment of FIGS. 4A-4D the connector assembly 142 includes two feedthrough pin banks 156, 158 and the terminal 190 of the connector block 146 is coupled to the feedthrough pin bank 158 by a conductor 192.

Figure 4A:
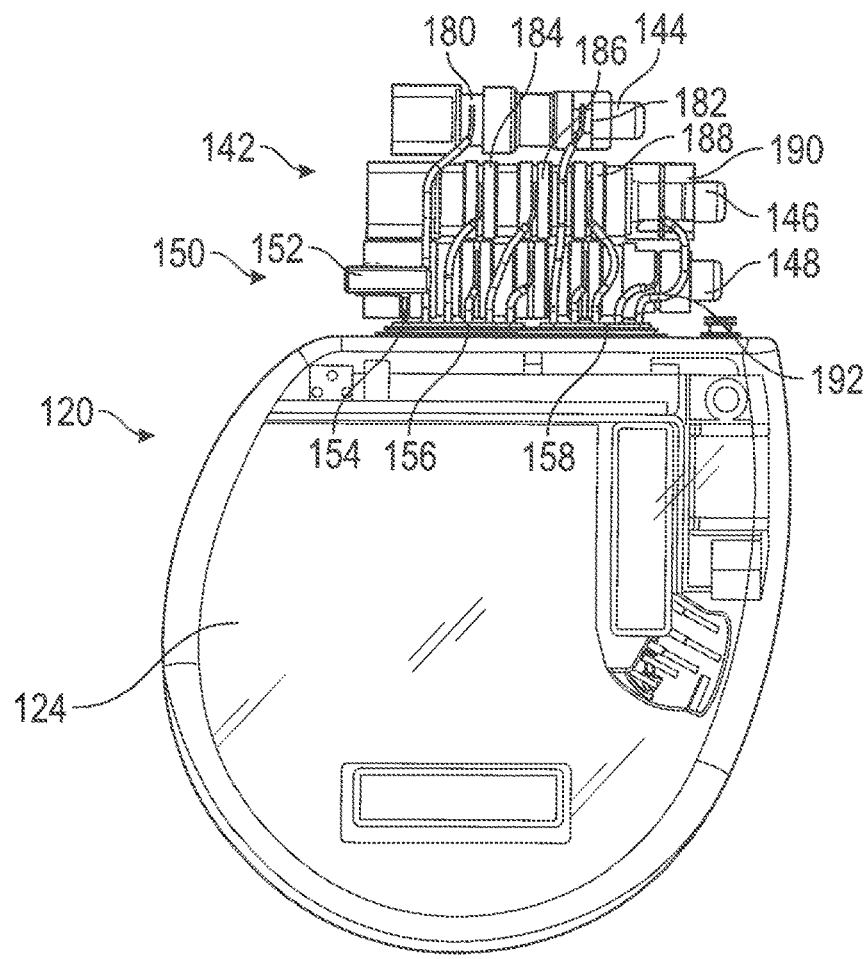
FIG. 4A is a side view of an implantable pulse generator including a second representative connector assembly and a second antenna assembly.
Figure 4B:
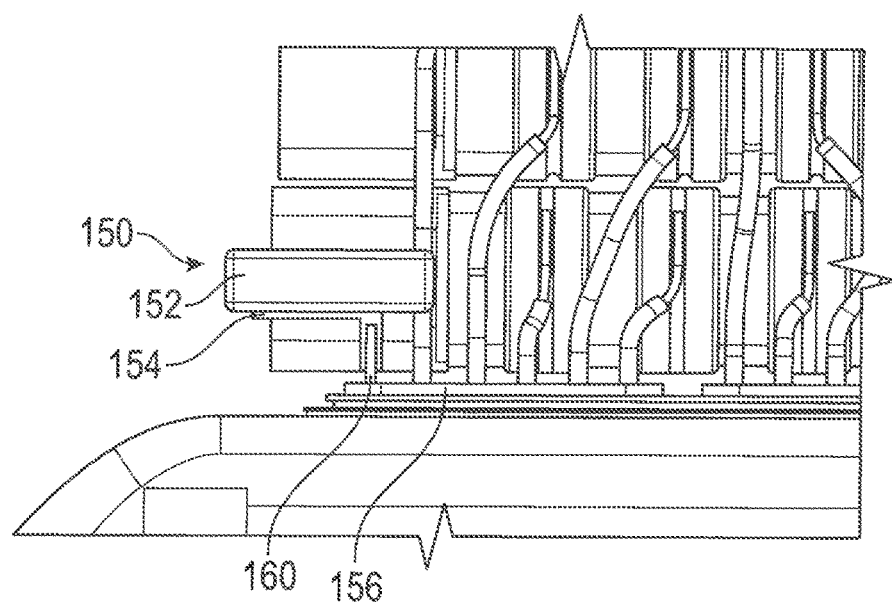
FIGS. 4B-4D are, respectively, an enlarged side view and two generally opposite isometric views of the second representative connector and antenna assemblies of FIG. 4A.
Figure 4C:
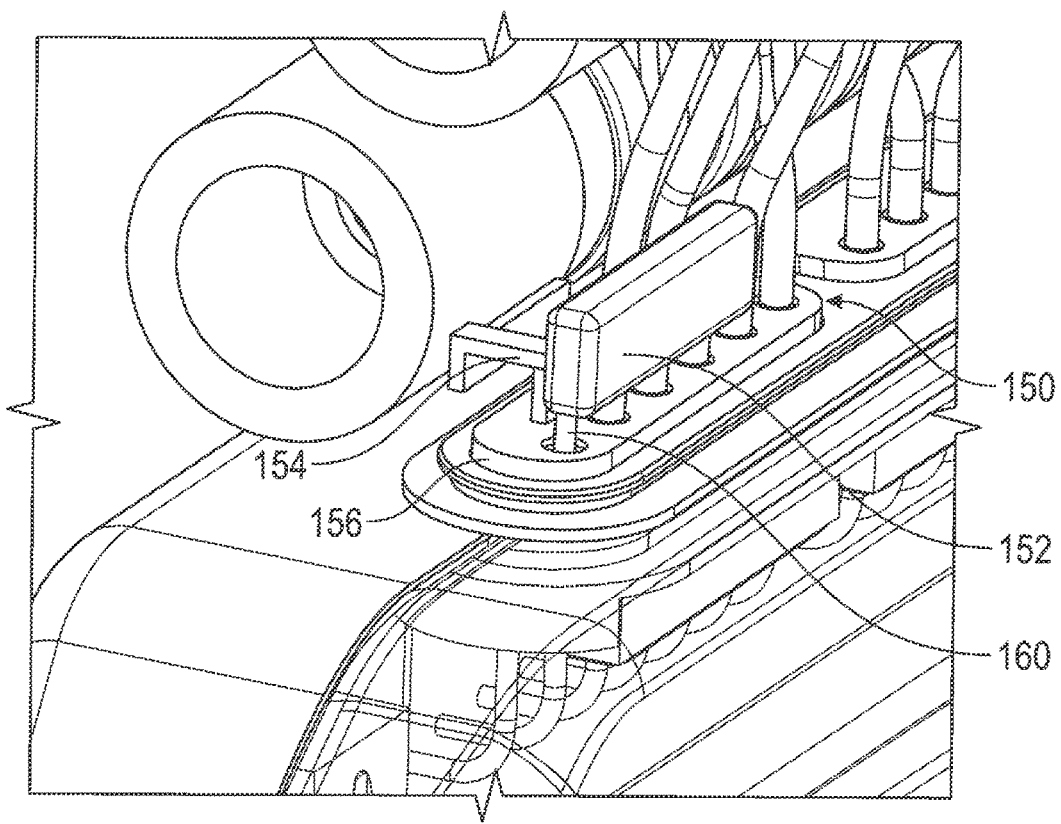
Figure 4D:
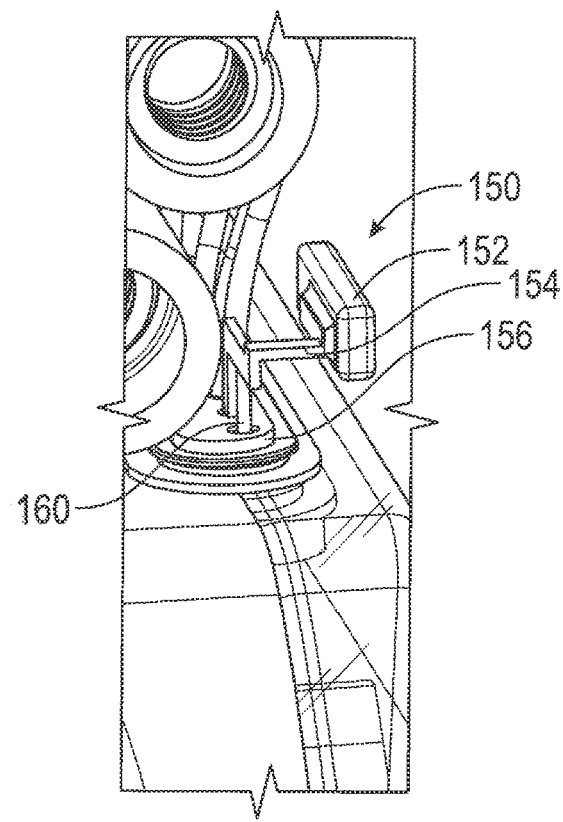

The connector assembly 142 further includes an antenna assembly 150 coupled to a pin of the feedthrough pin bank 156. The antenna assembly 150 includes an antenna 152 coupled to a mounting arm 154. As most clearly shown in FIGS. 4B-4D, the mounting arm 154 is coupled to a feedthrough pin 160 of the feedthrough pin bank 156. As shown in FIGS. 4C and 4D, the mounting arm 154 may then extend vertically and away from the feedthrough pin bank 156 such that the antenna 152 is positioned to avoid interference with the feedthrough pin bank 156, the connector blocks 144-148, or any conductors extending between the connector blocks 144-148 and the feedthrough pin bank 156.

Arrangements of the various components of the connector assembly 142 are not limited to that illustrated in FIGS. 4A-D. For example, placement of the antenna assembly 150 may vary based on the size and shape of the antenna assembly 150; the size, quantity, and arrangement of connector blocks within the connector assembly 142; the size, quantity and arrangement of feedthrough pin blocks within the connector assembly 142; and the quantity and routing of conductors extending between connector blocks and feedthrough pin blocks of the connector assembly 142.

Figure 5A:
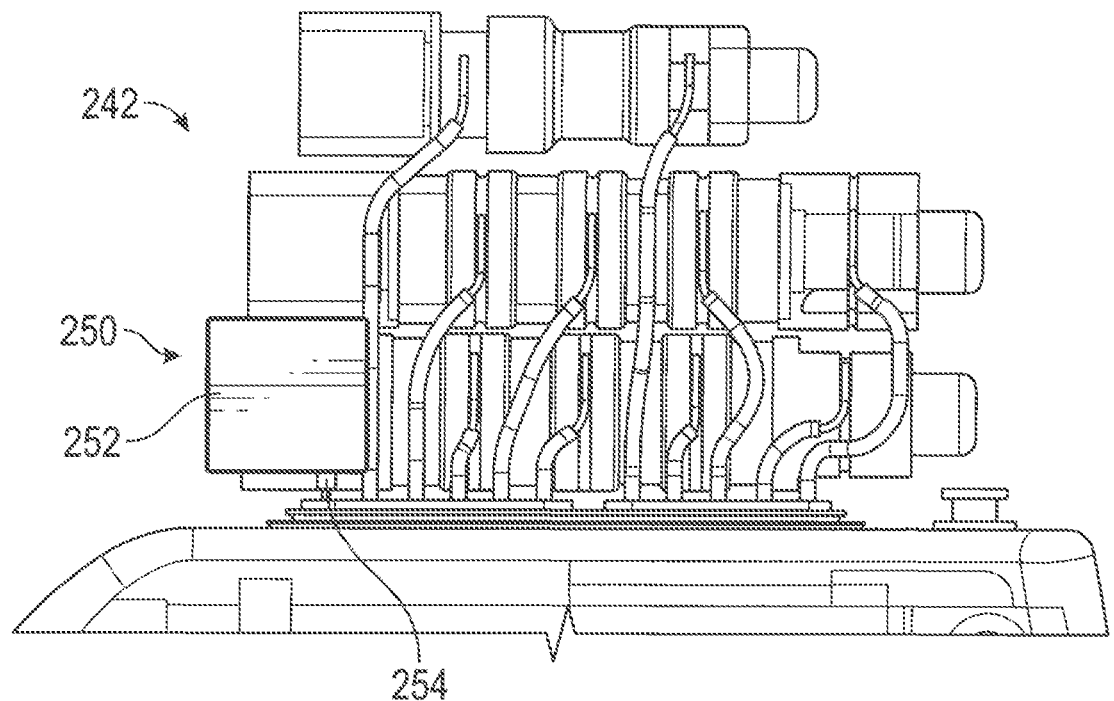
FIGS. 5A-5B are, respectively, a side view and an end view of a third connector assembly and a third antenna assembly.
Figure 5B:
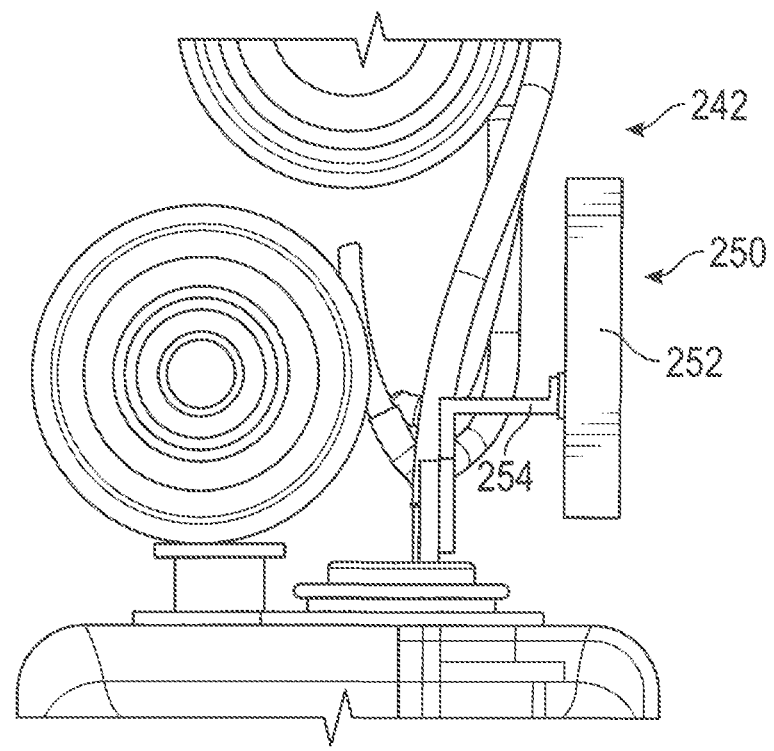
Figure 6A:
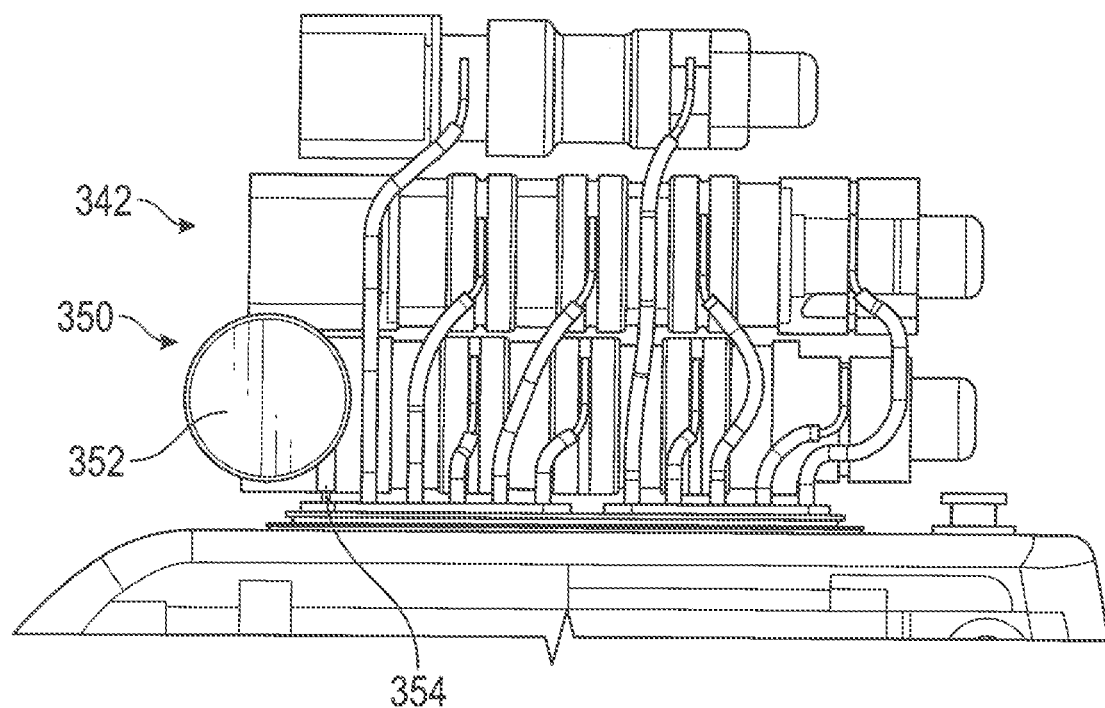
FIGS. 6A-6B are, respectively, a side view and an end view of a fourth connector assembly and a fourth antenna assembly.
Figure 6B:
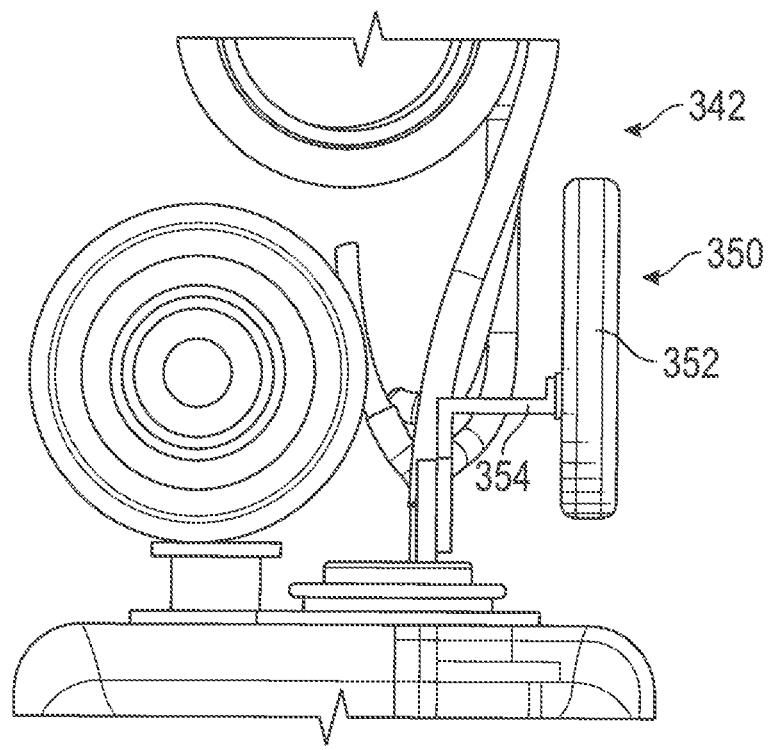

Although the antenna 152 of the antenna assembly 150 is generally shown as having an elongated or rectangular shape, other antenna shapes are possible. For example, FIGS. 5A-5B illustrate a connector assembly 242 including an antenna assembly 250. The antenna assembly 250 further includes a square antenna 252 coupled to a mounting arm 254. Similarly, FIGS. 6A-6B illustrate a connector assembly 342 including an antenna assembly 350 having a circular antenna 352 coupled to a mounting arm 354. Moreover, and as discussed in more detail below, while FIGS. 4A-7B include antennas arranged in a substantially vertical orientation, other orientations may be possible. For example, FIGS. 7-13 illustrate antennas having substantially horizontal orientations.

Figure 7:
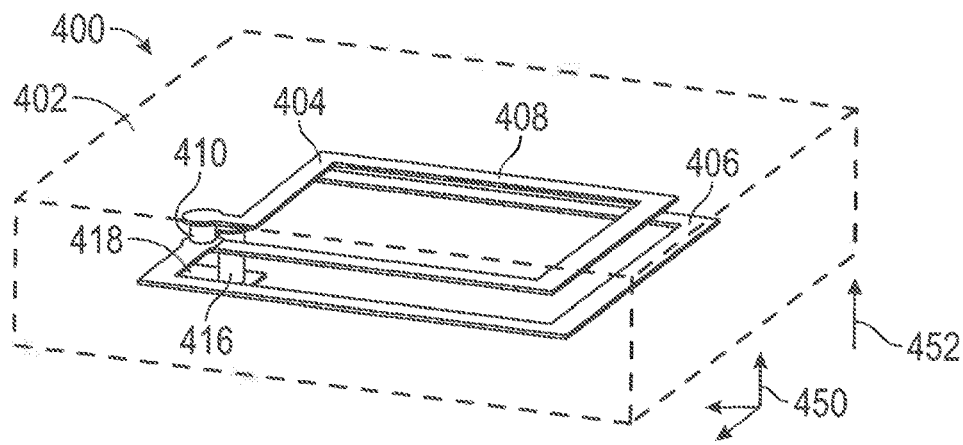
FIG. 7 is an isometric view of a generic antenna in accordance with this disclosure.

FIG. 7 is an illustration of an antenna 400 in accordance with this disclosure. The antenna 400 includes an antenna body 402 within which an antenna trace 404 is disposed. Although illustrated in FIG. 7 as having a rectangular shape, the antenna body 402 is not limited to a particular size or shape. Nevertheless, the antenna body 402 generally defines a longitudinal axis 450 and extends in a longitudinal direction 452.

The antenna trace 404 runs continuously through the antenna body 402 and is distributed across multiple layers within the antenna body 402. For example, the antenna trace 404 of FIG. 7 includes a first trace portion 406 in a first layer and a second trace portion 408 in a second layer, each of the first and second layers being transverse relative to the longitudinal axis 450 and offset from each other. The first trace portion 406 and second trace portion 408 are joined by an interlayer junction 410 extending substantially in the longitudinal direction 452. The antenna 400 may further include a terminal junction 416 disposed at an opposite end of the first trace portion 406 from the interlayer junction 410. The terminal junction 416 is further coupled to a plate 418 which may be coupled to a mounting arm or similar conductive structure to facilitate conduction of electrical signals to and from the antenna 400.

Figure 8A:
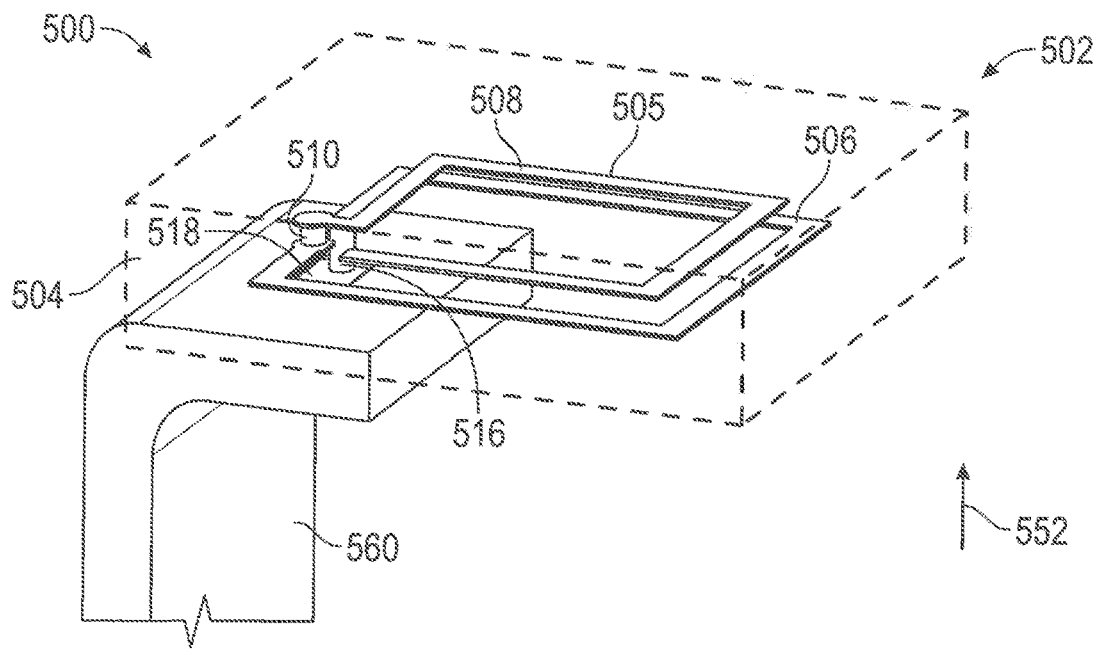
FIG. 8A is an isometric view of a fifth antenna assembly.
Figure 8B:
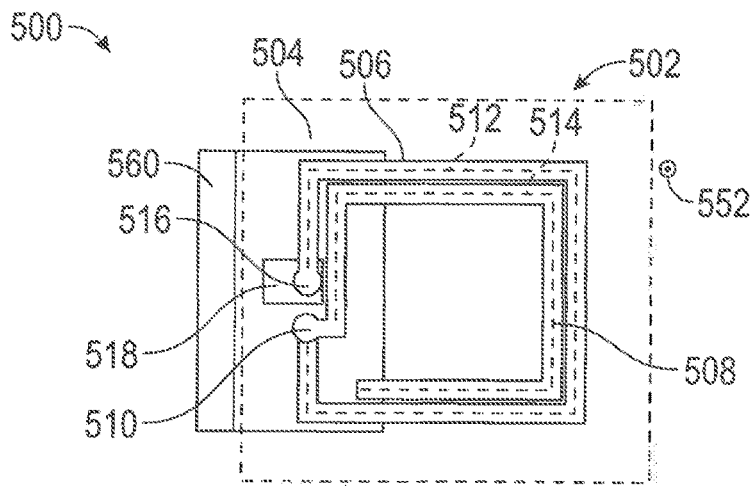
FIGS. 8B-8C are, respectively, a plan view and a side view of the antenna assembly of FIG. 8A.
Figure 8C:
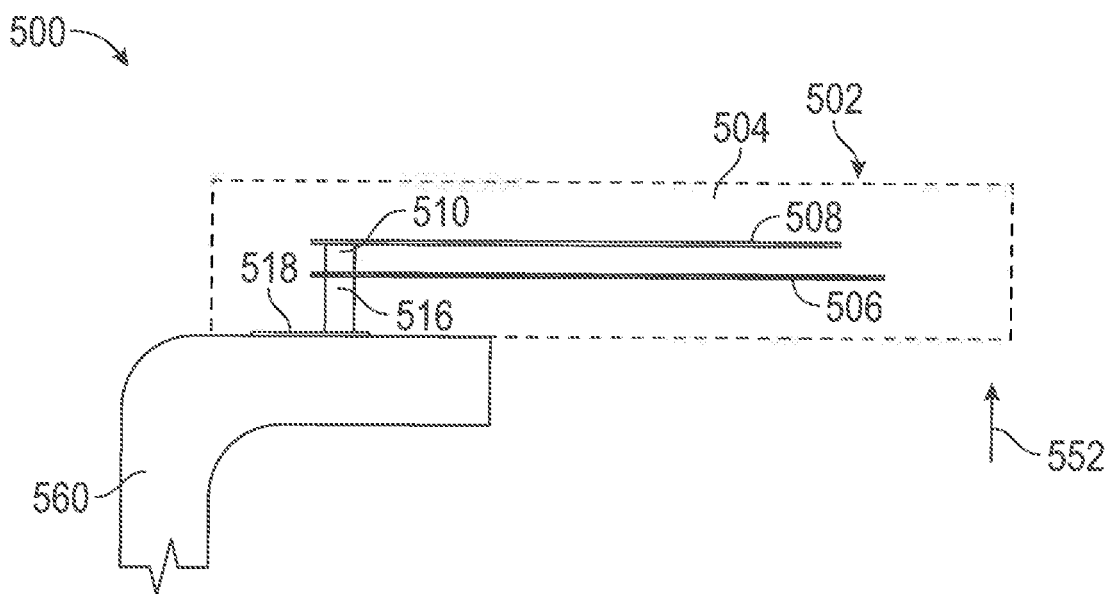

FIGS. 8A-8C illustrate an antenna assembly 500 including an antenna 502 and a mounting arm 560. The antenna 502 has a generally rectangular shape and includes an antenna body 504 within which an antenna trace 505 is disposed. The antenna 502 is coupled to the mounting arm 560 such that the antenna 502 is maintained in a substantially horizontal orientation. The antenna trace 505 includes a first trace portion 506 coupled to a second trace portion 508 by an interlayer junction 510. The first trace portion 506 and the second trace portion 508 are arranged in offset transverse layers relative to a longitudinal direction 552 along which the antenna body 504 extends.

The antenna body 504 is generally composed of one or more dielectric materials and the antenna trace 505 of one or more conductive materials. Antennas in accordance with this disclosure are generally implanted within a patient and, as a result, such materials may further be biocompatible. For example, the antenna body 504 may be composed of a ceramic or plastic including, without limitation, one or more of an alumina ceramic, a liquid crystal polymer, and a perovskite ceramic and the antenna trace 505 may be composed of one or more conductive metals including, without limitation, gold and platinum.

Referring to FIG. 8B, the first trace portion 506 and the second trace portion 508 define a first trace path 512 and a second trace path 514, respectively. The first trace path 512 and the second trace path 514 are arranged such that the first trace portion 506 and the second trace portion 508 are non-overlapping, thereby reducing capacitive coupling between the trace portions 506, 508. More generally, the first trace path 512 and the second trace path 514 are defined such that when arranged to be coplanar, the first trace path 512 defines a boundary within which the second trace path 512 is contained. Although the first trace path 512 and the second trace path 514 are shown in FIG. 8B as concentric squares, antennas in accordance with this disclosure are not limited to such arrangements and may include different and/or offset shapes in each transverse layer provided the second trace path 514 is contained within the boundary defined by the first trace path 512.

The first trace portion 506 may further be coupled to a terminal junction 516 extending from a conductive pad 518. The conductive pad 518 is in turn electrically coupled to the mounting arm 560. The mounting arm 560 is generally composed of a conductive material such that electrical signals can be transmitted between the antenna 502 and a feedthrough pin to which the mounting arm 560 is coupled.

Figure 9A:
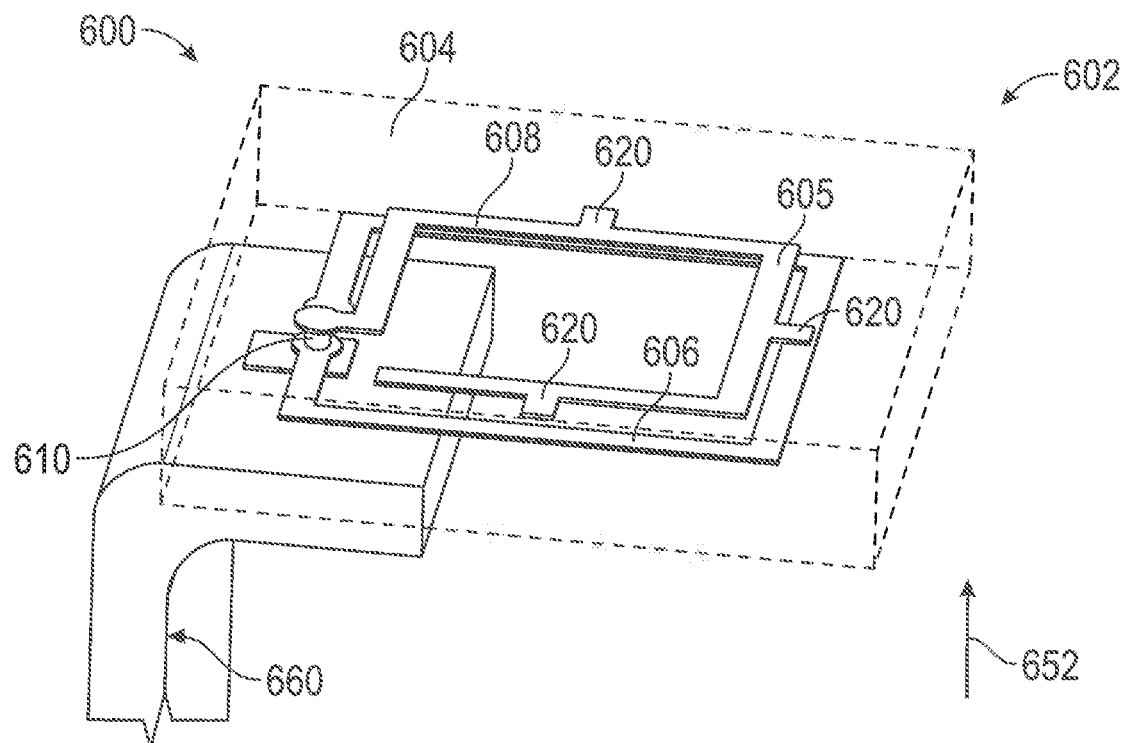
FIG. 9A is an isometric view of a sixth antenna assembly.
Figure 9B:
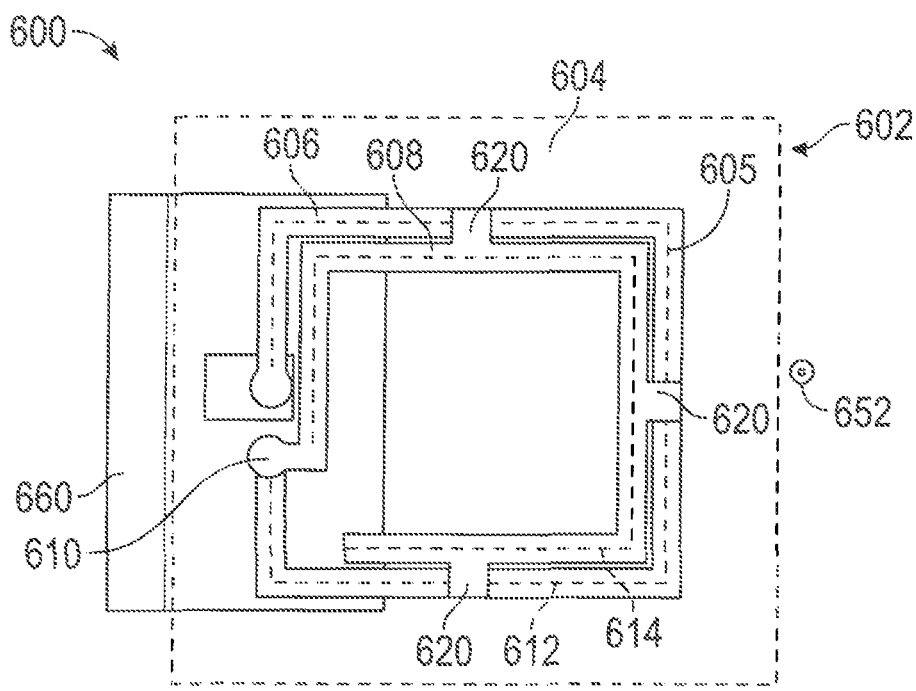
FIG. 9B is a plan view of the antenna assembly of FIG. 9A.

FIGS. 9A-9B illustrate an alternative antenna assembly 600 including an antenna 602 and a mounting arm 660. Similar to the antenna 500 of FIGS. 8A-8C, the antenna 602 has a generally rectangular shape and includes an antenna body 604 within which an antenna trace 605 is disposed. The antenna 602 is coupled to the mounting arm 660 such that the antenna 602 is maintained in a substantially horizontal orientation. The antenna trace 605 includes a first trace portion 606 coupled to a second trace portion 608 by an interlayer junction 610. The first trace portion 606 and the second trace portion 608 are arranged in offset transverse layers relative to a longitudinal direction 652 along which the antenna body 604 extends.

Referring to FIG. 9B, the first trace portion 606 and the second trace portion 608 define a first trace path 612 and a second trace path 614, respectively. The first trace path 612 and the second trace path 614 are arranged such that they are generally non-overlapping. However, in contrast to the implementation illustrated in FIGS. 8A-8C, the second trace portion 608 further includes a plurality of capacitive features extending from the second trace portion 608 to selectively overlap the first trace portion 606. More specifically, tabs 620 extend from the second trace portion 608 to overlap the first trace portion 606. As a result, capacitive structures are formed in which the tabs 620 form a first set of plates, corresponding sections of the first trace portion 606 form a second set of plates opposite the first set of plates, and the dielectric material of the antenna body 604 provides the dielectric material disposed between the two sets of plates.

The capacitive structures of the antenna 602 cause the antenna 602 to be the equivalent of multiple parallel capacitors with each capacitor corresponding to a single pair of a tab 620 and corresponding section of the first trace portion 606. As a result, the performance characteristics of the antenna 602 can be modified or tuned by adjusting the capacitance of the tab 620 and first trace portion 606 pairings. For example, capacitance may be tuned by one or more of modifying the offset between the first trace portion 604 and the second trace portion 606 (thereby modifying the distance between the tabs 620 and the first trace portion 606), changing the material of the antenna body 604 (thereby modifying the dielectric constant of the material disposed between the tabs 620 and the first trace portion 606), and changing the amount of overlapping area between the tabs 620 and the first trace portion 606. Notably, while the material of the antenna body 604 and the spacing between the first and second trace portions 604, 606, affect all tabs 620, the overlapping area of each tab 620 may be individually adjusted, thereby facilitating fine tuning of the capacitance of the antenna 602.

While the capacitive features of FIGS. 9A-9B are substantially square tabs 620 extending from the second trace portion 606, other shapes, sizes, and arrangements of the capacitive features are possible. For example, in certain implementations, capacitive features, such as tabs, may extend from the first trace portion 604 to overlap with the second trace portion 606. As another example, the capacitive feature may include a branch or bend extending from one of the first trace portion 604 and the second trace portion 606 to overlap the second trace portion 606 and the first trace portion 604, respectively. Moreover, any suitable quantity of capacitive features may be included to achieve the required tuning of the antenna 602.

Figure 10:
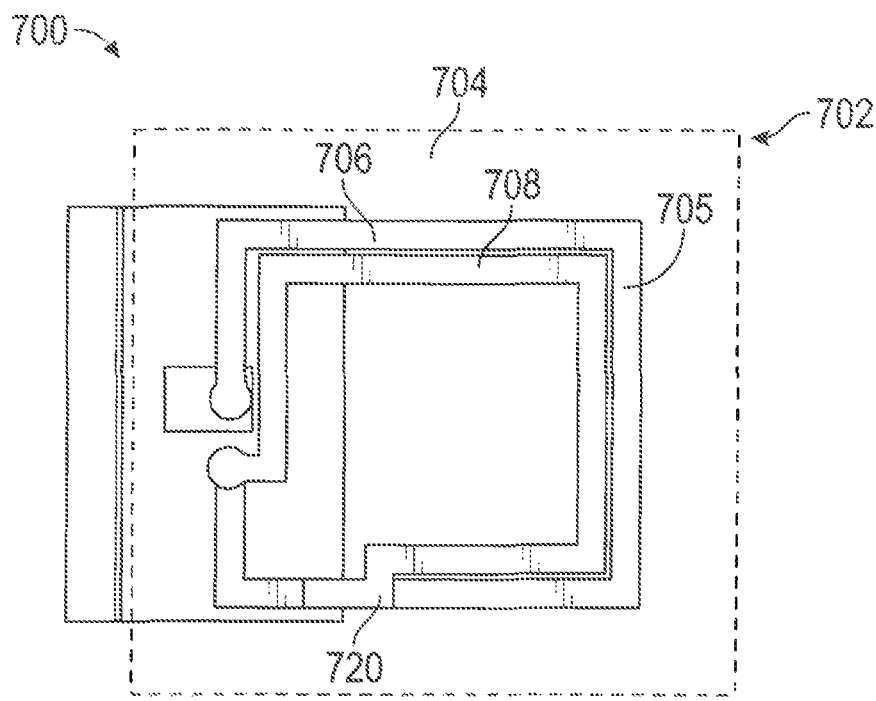
FIG. 10 is a plan view of a seventh antenna assembly.

FIG. 10 is a plan view of another example antenna assembly 700 that includes an antenna 702. The antenna includes an antenna trace 705 disposed within an antenna body 704. The antenna trace includes a first trace portion 706 disposed in a first transverse layer and a second trace portion 708 disposed in a second transverse layer that is offset from the first transverse layer. The antenna 702 includes a capacitive feature 720 extending from the second trace portion 708 to overlap with the first trace portion 706. More specifically, and in contrast to the tabs 620 shown in FIGS. 9A-9B, the capacitive feature 720 is in the form of an offshoot extending from the terminal end of the second trace portion 708. The offshoot 720 overlaps with a portion of the first trace portion 706, thereby creating a capacitive structure in which the offshoot forms a first plate, the opposite portion of the first trace portion 706 forms a second plate, and the material of the antenna body 704 acts as the dielectric between the first and second plates. By modifying the offshoot 720, the capacitance of the capacitive structure can be adjusted to tune the antenna 702. For example, the capacitance may be modified by changing the extent to which the offshoot 720 extends along the first trace portion 706.

Figure 11A:
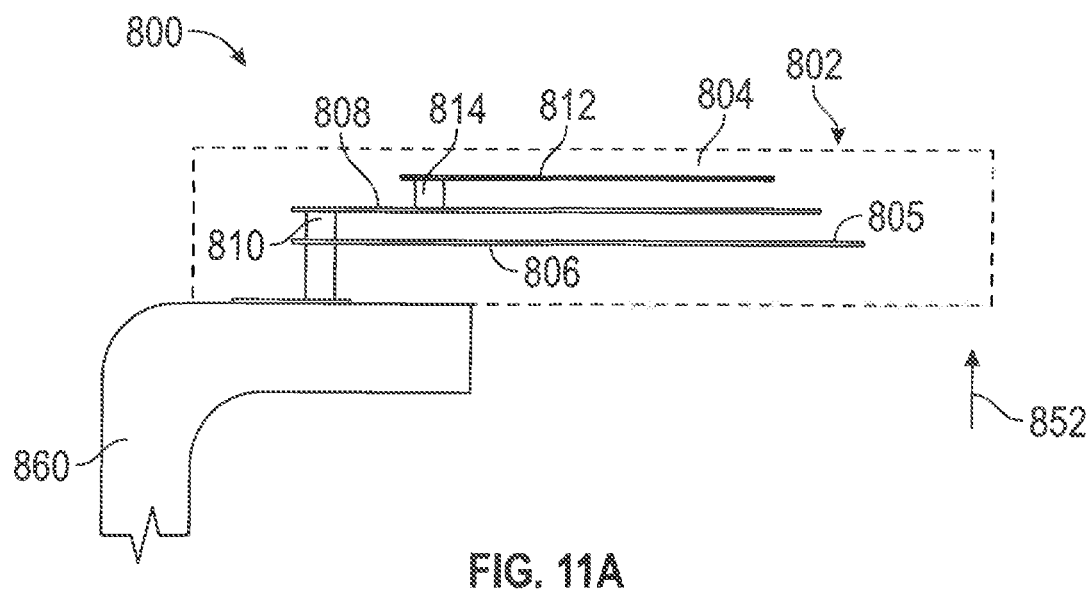
FIG. 11A is a side view of an eighth antenna assembly.
Figure 11B:
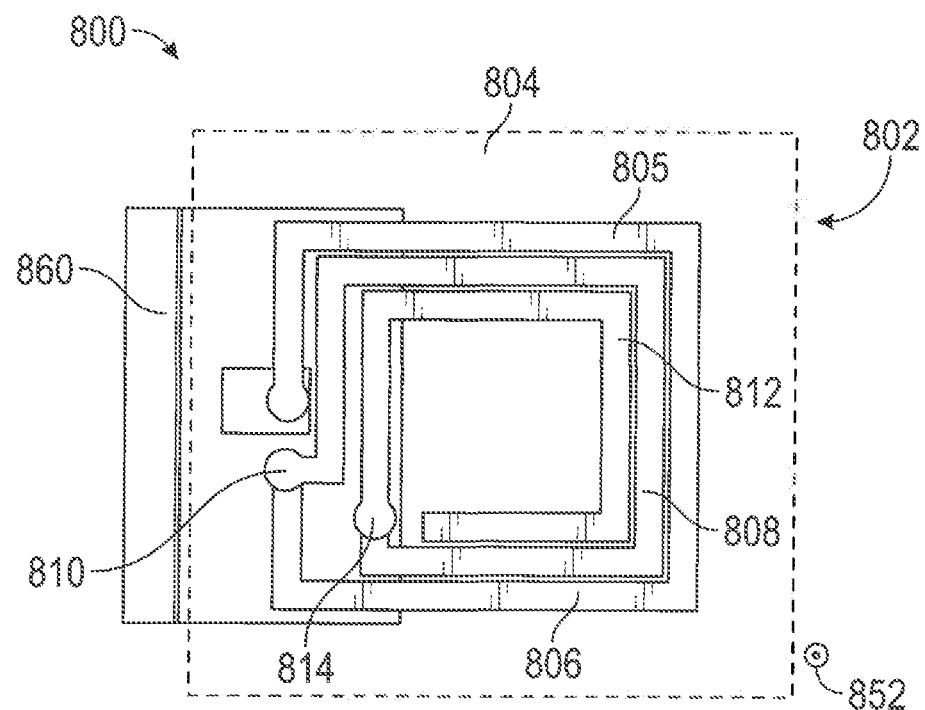
FIGS. 11B-11C are, respectively, a plan view and an isometric view of the antenna assembly of FIG. 11A.
Figure 11C:
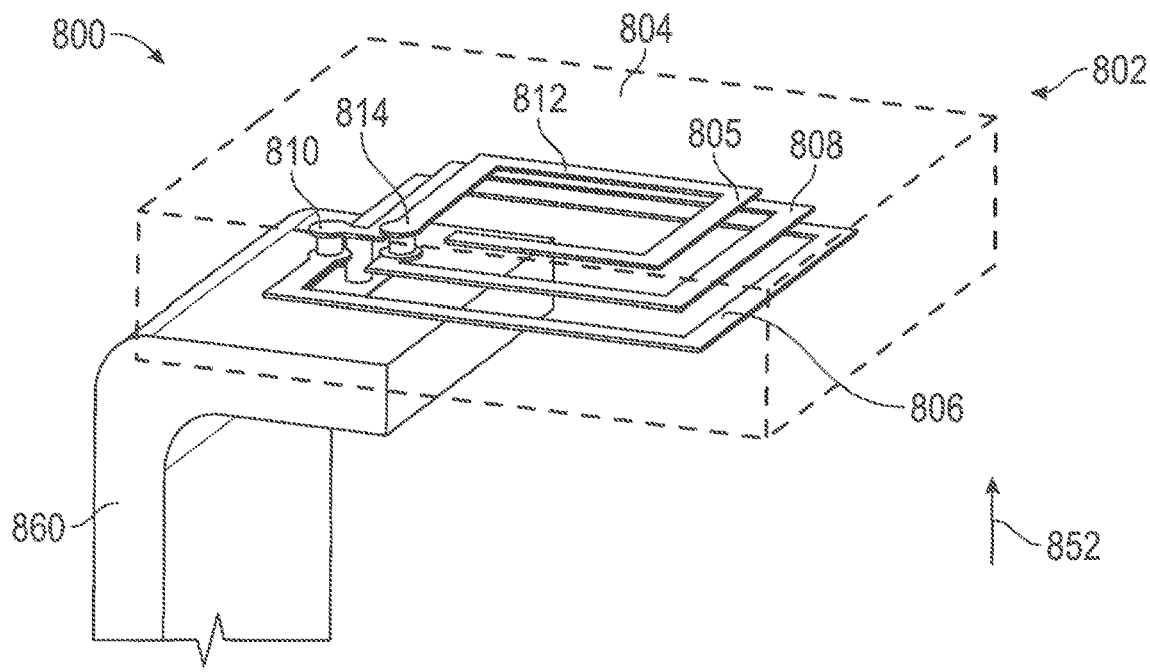

FIGS. 11A-11C illustrate yet another antenna assembly 800 in accordance with the present disclosure. The antenna assembly 800 includes an antenna 802 coupled to a mounting arm 860. The antenna 802 includes an antenna body 804 within which an antenna trace 805 is disposed. The antenna trace 805 includes a first trace portion 806 coupled to a second trace portion 808 by a first interlayer junction 810 and further includes a third trace portion 812 coupled to the second trace portion 808 by a second interlayer junction 814. The trace portions 806-810 are arranged in offset transverse layers relative to a longitudinal direction 852 along which the antenna body 804 extends.

FIGS. 11A-11C are intended to illustrate that antennas in accordance with this disclosure may include any suitable number of layered trace portions. For example and with reference to FIG. 11B, the trace portions 806-810 define trace paths 816-820, respectively. Each of the trace paths 816-820 are arranged such that the corresponding trace portions 806-810 are non-overlapping. More specifically, the first trace path 816 and the second trace path 818 are defined such that when arranged to be coplanar, the first trace path 818 defines a boundary within which the second trace path 818 is contained. Similarly, the second trace path 818 and the third trace path 820 are defined such that when arranged to be coplanar, the second trace path 818 defines a boundary within which the third trace path 820 is contained. Capacitive features (not shown), such as tabs, offshoots, and the like, may extend from any of the trace portions 806-810 to overlap and selectively form capacitive structures with others of the trace portions 806-810, thereby facilitating tuning of the antenna 802.

Figure 12A:
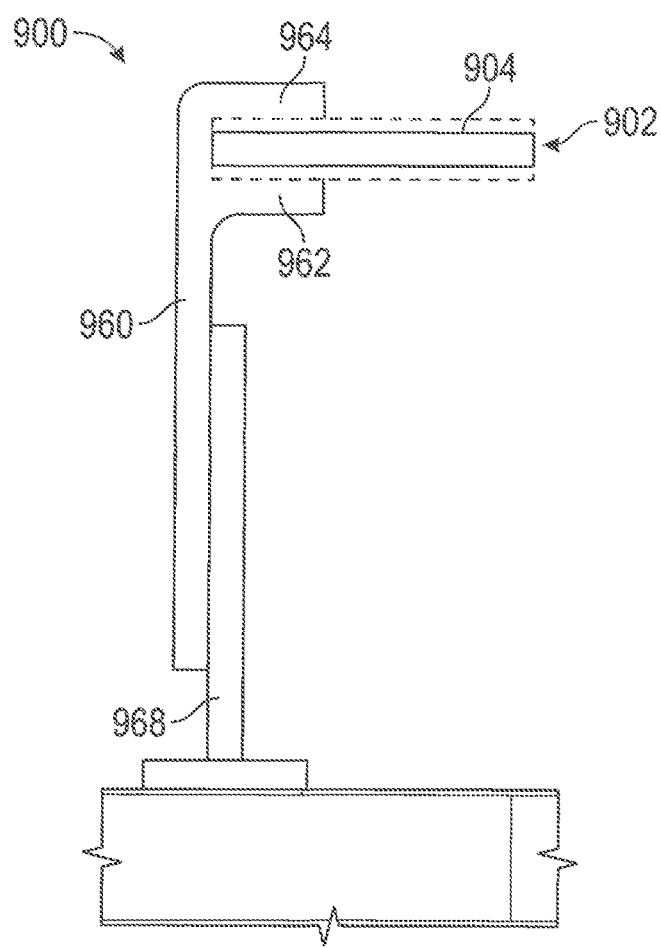
FIGS. 12A-12B are, respectively, a side view and an enlarged side view of a ninth antenna assembly.
Figure 12B:
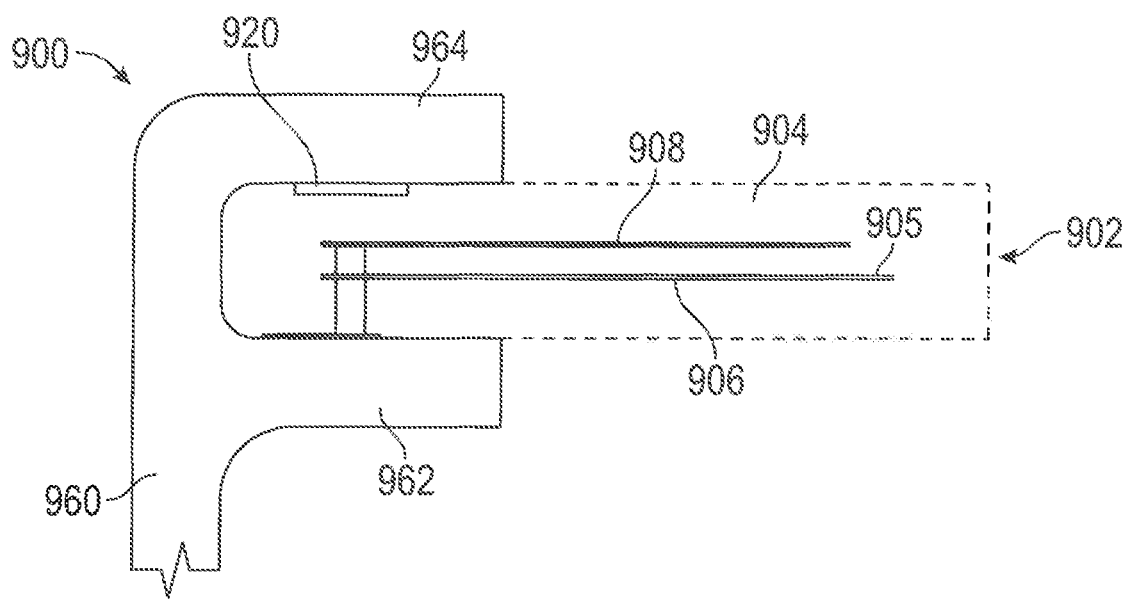
Figure 12C:
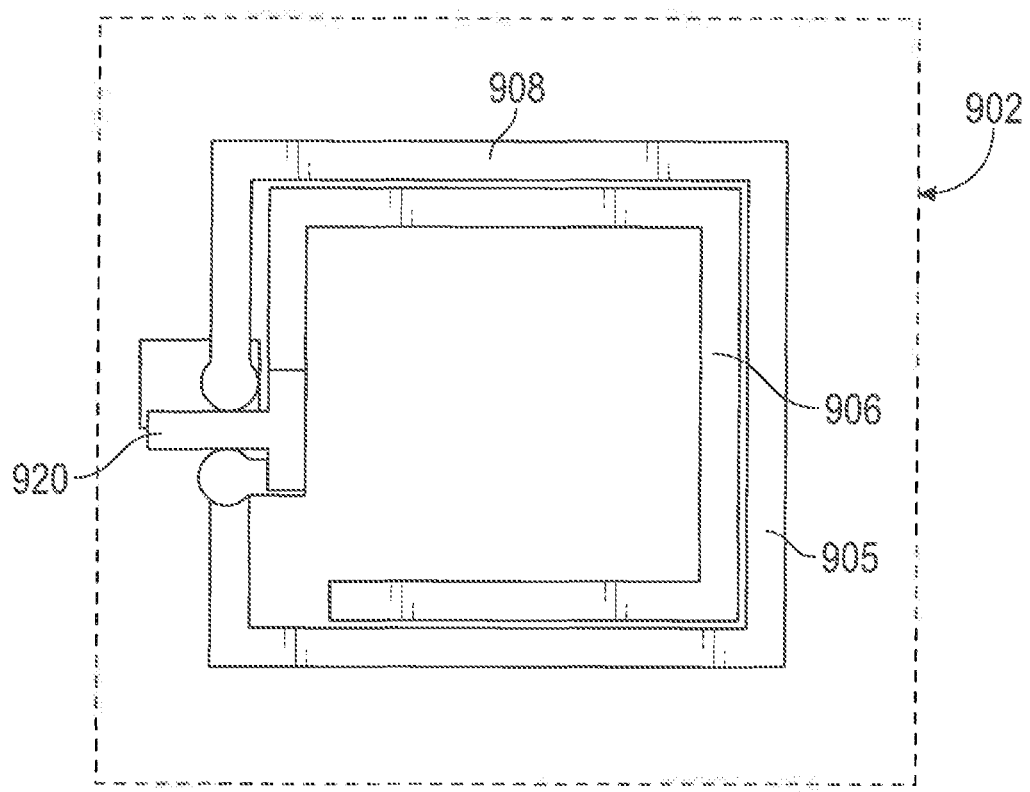
FIG. 12C is a plan view of an antenna of the antenna assembly of FIGS. 12A-12B.

FIGS. 12A-12C depict another antenna assembly 900 in accordance with the present disclosure. The antenna assembly 900 includes an antenna 902 coupled to a mounting arm 960. The antenna includes an antenna body 904 within which an antenna trace 905 (shown in FIGS. 12B-12C) is disposed. The antenna trace 905 includes a first trace portion 906 and a second trace portion 908 disposed on an offset layer from the first trace portion 906 within the antenna body 904. The first trace portion 906 and the second trace portion 908 are shown as being non-overlapping such that capacitive coupling between the first trace portion 906 and the second trace portion 908 is minimized. In certain implementations, the first trace portion 906 and/or the second trace portion 908 may include tabs or similar capacitive features that overlap the second trace portion 908 and the first trace portion 906, respectively.

The mounting arm 960 is composed of a conductive material and includes a first coupling portion 962 and a second coupling portion 964 that extend over opposite portions of the antenna 902. As shown in FIG. 12B, the first coupling portion 962 is in contract with the antenna trace 905 and, more specifically, with a terminal plate 966 of the antenna trace 905, thereby facilitating electrical conduction between the antenna 902 and a feedthrough pin 968 to which the mounting arm 960 is coupled.

Disposed between the second coupling portion 964 and the antenna trace 905 is a capacitive feature 920 in the form of a plate 920. The plate 920 is in contact with the second coupling portion 964 and overlapping a portion of the second trace portion 908. In other implementations, the plate 920 may be shaped and positioned to overlap a different portion of the antenna trace 905, such as the first trace portion 906. The plate 920 may be integrated into either of the second coupling portion 964 and the antenna body 904 or may be a separate component disposed between the second coupling portion 964 and the antenna body 904. As more clearly illustrated in FIG. 9C, which excludes the mounting arm 960, the plate 920 is positioned to overlap a portion of the second coupling portion 964, thereby forming a capacitive structure that may be used to tune the antenna 902. More specifically, the plate 920 forms a first capacitor plate, the portion of the second trace portion 908 forms a second capacitor plate, and the antenna body 904 acts as the dielectric material between the two plates.

Figure 13:
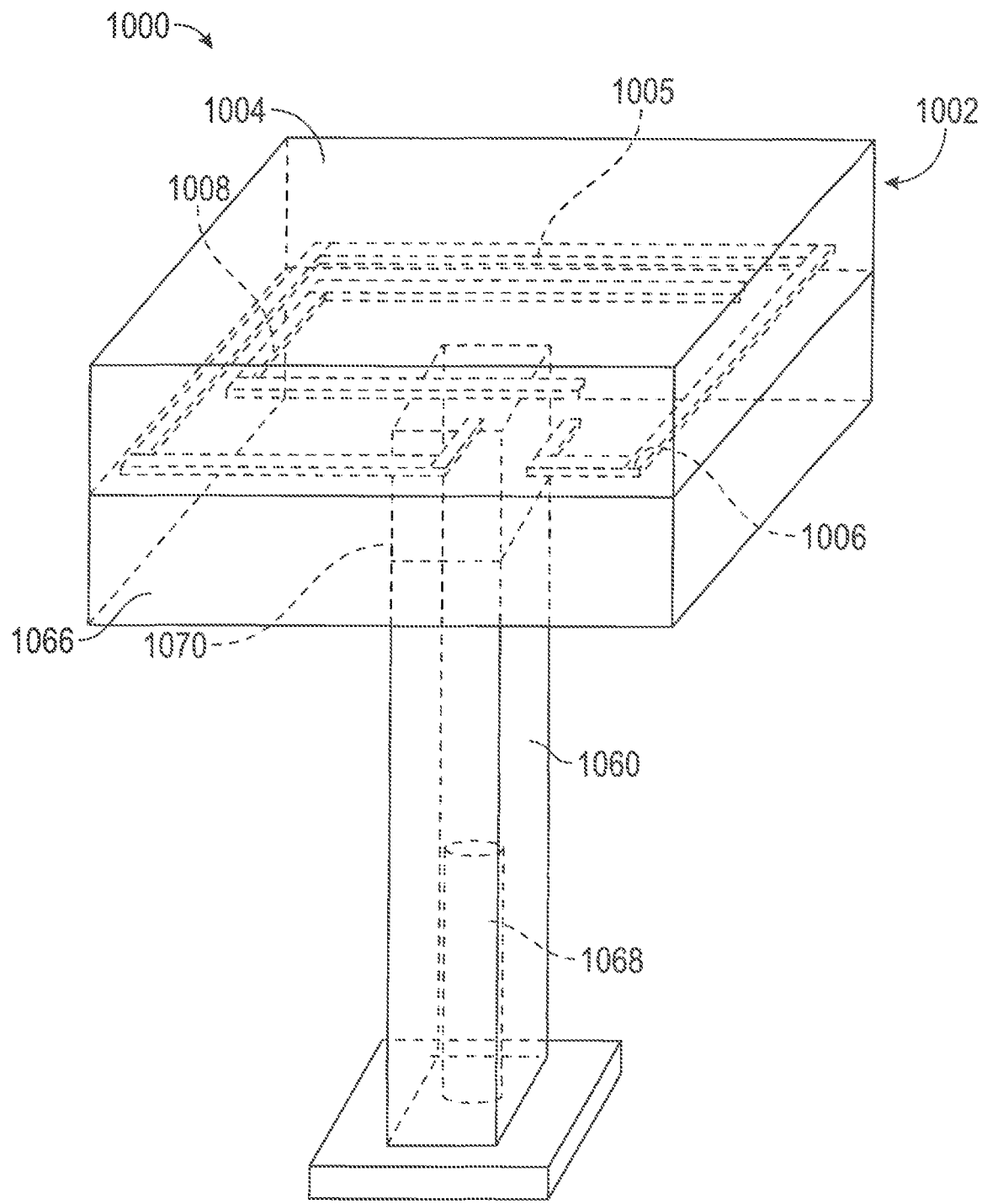
FIG. 13 is an isometric view of a tenth antenna assembly.

FIG. 13 illustrates another embodiment of an antenna assembly 1000 in accordance with this disclosure. The antenna assembly 1000 includes an antenna 1002 coupled to a mounting arm 1060 by an antenna shroud 1066.

The antenna 1002 includes an antenna body 1004 composed of a dielectric material and an antenna trace 1005 disposed within the antenna body 1004. The antenna trace 1005 includes a first antenna portion 1006 and a second trace portion 1008. The first trace portion 1006 and the second trace portion 1008 are disposed in offset transverse layers within the antenna body 1004 and are arranged such that the second trace portion 1008 is disposed within a boundary defined by the first trace portion 1006. Additional trace portions may also be included within the antenna body 1004, with each successive trace portion being disposed within a boundary defined by the previous layer. Any trace portion may include capacitive features shaped and positioned to overlap a portion of an adjacent trace portion. For example, although not depicted in FIG. 13, either of the first trace portion 1006 and the second trace portion 1008 may include capacitive features that extend and overlap the second trace portion 1008 and the first trace portion 1006, respectively. By varying the quantity, placement, and size of the capacitive features, the antenna 1002 may be tuned to improve its response to signals in particular frequencies.

The mounting arm 1060 is conductive and is coupled to the antenna trace 1005. The mounting arm 1060 is adapted to be coupled to a feedthrough pin 1068 of an IPG (not shown) and to communicate signals between the antenna trace 1005 and the feedthrough pin 1068. Coupling of the mounting arm 1060 to the antenna trace 1005 is achieved through the antenna shroud 1066, which is coupled to each of the antenna 1002 and the mounting arm 1060 such that the mounting arm 1060 is maintained in contact with the antenna trace 1005. More specifically, the antenna shroud 1066 includes a surface to which the antenna 1002 is coupled. Coupling of the antenna shroud 1066 to the antenna 1002 may be achieved in various ways including, without limitation, fusing the antenna shroud 1066 to the antenna 1002 using a co-firing process. The antenna shroud 1066 further defines a receptacle 1070 into which the mounting arm 1060 is inserted. The receptacle 1070 extends through the antenna shroud 1066 such that, when inserted into the receptacle 1070, the tip of the mounting arm 1060 contacts and electrically couples with the antenna trace 1005. The tip of the mounting arm 1060 (and the mounting arm 1060 more generally) as well as the receptacle 1070 may have a variety of mating shapes and are not limited to the substantially rectangular shapes shown in FIG. 13. Moreover, in certain implementations, the tip of the mounting arm 1060 and the receptacle 1070 may be tapered or otherwise vary in shape along their lengths.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. An implantable electronic device comprising:
   a hermetically sealed housing containing an electrical circuit adapted to generate and receive radio frequency (RF) signals;
   an antenna assembly comprising an antenna defining a longitudinal axis, the antenna comprising:
      a dielectric antenna body extending along the longitudinal axis; and
      an antenna trace disposed within the dielectric antenna body, the antenna trace comprising:
         a first trace portion disposed in a first transverse layer and defining a first trace path;
         a second trace portion disposed in a second transverse layer longitudinally offset from the first transverse layer and defining a second trace path; and
         a junction extending longitudinally, at least in part, and electrically coupling the first trace portion to the second trace portion, and
      a conductive mounting arm coupled to each of the electrical circuit and the dielectric antenna body such that the conductive mounting arm forms a conductive path between the electrical circuit and the antenna trace and supports the dielectric antenna body at an offset from the housing;
   wherein, if projected to be coplanar, the first trace path defines a trace boundary and the second trace path is within the trace boundary.

2. The implantable electronic device of claim 1, wherein the antenna further comprises a capacitive feature extending from at least one of the first trace portion or the second trace portion and at least partially overlapping the second trace portion or the first trace portion, respectively, with a portion of the antenna body disposed therebetween.

3. The implantable electronic device of claim 2, wherein the capacitive feature includes a tab extending from the at least one of the first trace portion or the second trace portion.

4. The implantable electronic device of claim 1, wherein:
   the dielectric antenna body comprises at least one first biocompatible material; and
   the antenna trace comprises at least one second biocompatible material.

5. The implantable electronic device of claim 4, wherein:
   the first biocompatible material is selected from a first group including alumina ceramic, liquid crystal polymer, and perovskite ceramic; and
   the second biocompatible material is selected from a second group including gold and platinum.

6. The implantable electronic device of claim 1, wherein the implantable electronic device includes a feedthrough pin coupled to the electrical circuit and extending through the housing, the mounting arm being electrically coupled to each of the antenna trace and the feedthrough pin.

7. The implantable electronic device of claim 6, wherein the antenna includes a transverse surface and the mounting arm includes a coupling feature extending across the transverse surface.

8. The implantable electronic device of claim 7 further comprising a capacitive feature disposed between the coupling feature and the transverse surface, the coupling feature positioned to overlap one of the first trace portion and the second trace portion with a portion of the antenna body disposed therebetween.

9. The implantable electronic device of claim 6 further comprising a shroud coupled to each of the antenna body and the mounting arm, the shroud defining a receptacle into which a terminal end of the mounting arm is inserted.

10. The implantable electronic device of claim 1, wherein the antenna trace further comprises:
    a third trace portion disposed in a third transverse layer such that the second transverse layer is disposed between the first transverse layer and the third transverse layer, the third trace portion defining a third trace path; and
    a second junction extending longitudinally, at least in part, and coupling the second trace portion to the third trace portion,
    wherein, if projected to be coplanar, the second trace path defines a second trace boundary within the trace boundary defined by the first trace path and the third trace path is within the second trace boundary.

11. An implantable electronic device comprising:
    a hermetically sealed housing containing an electrical circuit adapted to generate and receive radio frequency (RF) signals; and
    an antenna assembly electrically coupled to the electrical circuit, the antenna assembly comprising:
       a dielectric antenna body defining a longitudinal axis;
       an antenna trace arranged in a plurality of transverse trace layers within the dielectric antenna body, the plurality of trace layers shaped and arranged to reduce capacitive coupling between the trace layers relative to an arrangement in which all trace layers overlap;
       at least one capacitive feature, each capacitive feature overlapping a respective portion of the antenna trace such that a corresponding portion of the antenna body is disposed therebetween, and
       a conductive mounting arm coupled to each of the electrical circuit and the dielectric antenna body such that the conductive mounting arm forms a conductive path between the electrical circuit and the antenna trace and supports the dielectric antenna body at an offset from the housing.

12. The implantable electronic device of claim 11, wherein the at least one capacitive feature extends from a first layer of the plurality of trace layers and overlaps a second layer of the plurality of trace layers.

13. The implantable electronic device of claim 11, wherein the implantable electronic device further comprises a feedthrough pin coupled to the electrical circuit and extending through the housing, the mounting arm being electrically coupled to each of the antenna trace and the feedthrough pin.

14. The implantable electronic device of claim 13, wherein the at least one capacitive feature includes a plate coupled to the mounting arm.

15. The implantable electronic device of claim 11, wherein each trace layer of the plurality of trace layers defines a respective trace path and a respective trace boundary and the plurality of trace layers is ordered such that, if projected to be coplanar, each respective trace path other than that of a first trace layer is within the respective trace boundary of a preceding trace layer.

\* \* \* \* \*